(12) United States Patent
Hamacher et al.

(10) Patent No.: US 9,802,044 B2
(45) Date of Patent: Oct. 31, 2017

(54) SYSTEM AND METHOD FOR NEURAL HEARING STIMULATION

(71) Applicant: Advanced Bionics AG, Stäfa (CH)

(72) Inventors: Volkmar Hamacher, Hannover (DE); Josef Chalupper, Paunzhausen (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/895,658

(22) PCT Filed: Jun. 6, 2013

(86) PCT No.: PCT/EP2013/061652
§ 371 (c)(1),
(2) Date: Dec. 3, 2015

(87) PCT Pub. No.: WO2014/194950
PCT Pub. Date: Dec. 11, 2014

(65) Prior Publication Data
US 2016/0136425 A1  May 19, 2016

(51) Int. Cl.
*A61N 1/36* (2006.01)
*A61N 1/05* (2006.01)
*H04R 25/00* (2006.01)

(52) U.S. Cl.
CPC ....... *A61N 1/36032* (2013.01); *A61N 1/0541* (2013.01); *H04R 25/405* (2013.01);
(Continued)

(58) Field of Classification Search
CPC .... A61N 1/36032; A61N 1/05; A61N 1/0541; H04R 25/70; H04R 2225/43;
(Continued)

(56) References Cited

U.S. PATENT DOCUMENTS

| | | |
|---|---|---|
| 8,285,383 B2 | 10/2012 | van Dijk et al. |
| 8,422,706 B2 | 4/2013 | Kulkarni et al. |

(Continued)

FOREIGN PATENT DOCUMENTS

| | | |
|---|---|---|
| EP | 2 262 285 A1 | 12/2010 |
| EP | 2 360 943 A1 | 8/2011 |
| WO | 2011/032021 A1 | 3/2011 |

*Primary Examiner* — Deborah Malamud
(74) *Attorney, Agent, or Firm* — ALG Intellectual Property, LLC (57) ABSTRACT

A system for stimulation of a patient's ipsilateral cochlea, having at least two spaced apart patient-worn microphones for providing first and second audio signals from ambient sound; a sound processor for generating an ipsilateral auditory nerve stimulation signal in a plurality of output channels from at least one of the input audio signals; and a stimulation assembly for being implanted within the ipsilateral cochlea and having a plurality of stimulation channels for ipsilateral stimulation of the patient's hearing according to the ipsilateral auditory nerve stimulation signal. The sound processor comprising a DOA unit for determining periodically a main direction of incidence of ambient sound from a sound source by analyzing the first and second audio signals, and a directional information coding unit for coding information concerning the determined main direction of incidence in the ipsilateral auditory nerve stimulation signal in manner to enable the patient to localize the sound source.

28 Claims, 5 Drawing Sheets

(52) U.S. Cl.
CPC .......... *H04R 25/407* (2013.01); *H04R 25/48* (2013.01); *H04R 25/606* (2013.01); *H04R 2225/43* (2013.01)

(58) Field of Classification Search
CPC .. H04R 25/606; H04R 25/505; A61B 5/4005; A61B 5/486; A61B 5/6803; A61B 5/686
See application file for complete search history.

(56) References Cited

U.S. PATENT DOCUMENTS

| | | |
|---|---|---|
| 8,503,704 B2 | 8/2013 | Francart et al. |
| 8,526,647 B2 | 9/2013 | Pedersen et al. |
| 8,953,817 B2 | 2/2015 | Mejia et al. |
| 2007/0016267 A1 | 1/2007 | Griffin et al. |
| 2009/0304187 A1 | 12/2009 | Dittberner |

SYSTEM AND METHOD FOR NEURAL HEARING STIMULATION

BACKGROUND OF THE INVENTION

Field of the Invention

The invention relates to a system and a method for neural stimulation of a patient's hearing, such as by cochlea stimulation.

Description of Related Art

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant (CI) systems) have been developed. auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Typically, the audio signal, which usually is captured by a microphone, is divided into a plurality of analysis channels, each containing a frequency domain signal representative of a distinct frequency portion of the audio signal, wherein the frequency domain signal in each analysis channel may undergo signal processing, such as by applying channel-specific gain to the signals. The processed frequency domain signals are used for generating certain stimulation parameters according to which the stimulation signals in each stimulation channel is generated. The analysis channels are linked to the stimulation channels via channel mapping. The number of stimulation channels may correspond to the number of analysis channels, or there may be more stimulation channels than analysis channels, or there may be more analysis channels than stimulation channels. Various stimulation strategies are used, such as current steering stimulation (in order to stimulate a stimulation site located in between areas associated with two or more electrodes) and N-of-M stimulation (wherein stimulation current is only applied to N of M total stimulation channels during a particular stimulation frame).

An example for such a CI system with electrical cochlea stimulation is described in International Patent Application Publication WO 2011/032021 A1 and corresponding U.S. Pat. No. 8,422,706.

Human sound source localization ability is mainly based on detection of interaural time or level differences (ILD/ITD) in the signals picked up by the two ears. In addition, the pinna provides for some monaural cues due to direction and elevation dependent changes of the frequency spectrum of the sound impinging onto the pinna. In general, CI users have difficulties to localize sound sources, since the ITDs are distorted by the CI signal processing.

In case of a unilateral CI usage the auditory system receives input only from the ear provided with the CI. Therefore, in such case the localization ability is very weak, since the direction dependent sound shaping of the pinna, at best, allows only for a very rough front/back differentiation or left/right differentiation.

In case of a bimodal fitting, in which an acoustic hearing aid is worn on the contralateral ear in addition to the CI provided at the ipsilateral ear, localization ability still is quite weak. Although bimodal fittings provide binaural input to the auditory system, localization cues (ILD/ITD) are still largely absent due to the usually only little overlap of the frequency range of the electrical stimulation and the frequency range of the acoustical stimulation (typically, the hearing aid stimulates the lower frequencies up to 1-1.5 kHz, while CI stimulation does not take place at frequencies below 1 kHz due to the limited insertion depth of the CI electrode).

In case of a CI fitting with routing of a microphone signal from a microphone positioned at the contralateral ear ("CROS" design), the localization ability is more or less lost, since the head shadow cue is no longer available due to the addition of a routed contralateral microphone signal to the ipsilateral microphone signal of the CI speech processor (such CROS systems are used for overcoming the head shadow in order to improve speech understanding in cases where speech comes from the non-implanted side).

U.S. Pat. No. 8,503,704 B2 relates to a binaural CI system, wherein the localization cues are modified in the neural stimulation signals in order to enhance the localization ability of the patient; for example, a detected localization cue, such as an interaural level difference (ILD), is transposed to a lower frequency.

U.S. Pat. No. 8,526,647 B2 relates to a hearing instrument, such as a CI, wherein directional cues may be artificially generated by frequency shaping based on information from a directional system in order to improve front/rear discrimination, with one microphone being located at each ear of the user.

U.S. Pat. No. 8,285,383 B2 relates to a CI system including directional sound processing by enhancing the sensitivity of at least one associated microphone to the desired sounds and essentially treating undesired sound as noise.

U.S. Pat. No. 8,953,817 B2 relates to a binaural beamformer to be used in CI devices, comprising a microphone at each side of the head, wherein a single channel output signal is produced by modifying the signals captured by the microphones in a manner so as to insert localization cues according to the head-related transfer functions to enable to user to perceive the direction of the sound, wherein the single channel output signal is supplied to both ears. The interaural time difference may be used to cancel relatively low frequency sounds, depending on the direction of incidence, and the interaural level difference can be used to cancel high frequency sounds depending on their direction of incidence in a weighted sum configuration. The system is concerned with improving directionality—but not localization—of a binaural hearing system, wherein a Wiener filter type blocking matrix is used to filter speech signals, with the weighted sum of filtered and direct signals being produced at each ear.

SUMMARY OF THE INVENTION

It is an object of the invention to provide for a cochlea stimulation system and method, wherein the localization ability of the patient is enhanced.

According to the invention, the subject is achieved by a system and a method as described herein.

The invention is beneficial in that, by determining a main direction of incidence of sound from a sound source and by coding information concerning the determined main direction of incidence in the ipsilateral auditory nerve stimulation system in a manner so as to render the directional information perceivable by the patient, the patient's localization ability is enhanced while avoiding the need for bilateral stimulation.

Primarily, the invention is to be used for unilateral CI systems which may include a contralateral CROS device or a contralateral acoustic hearing aid. However, the invention also may be applied to bilateral CI systems.

Hereinafter, examples of the invention will be described with reference to the accompanying drawings:

DETAILED DESCRIPTION OF THE INVENTION

Figure 1:
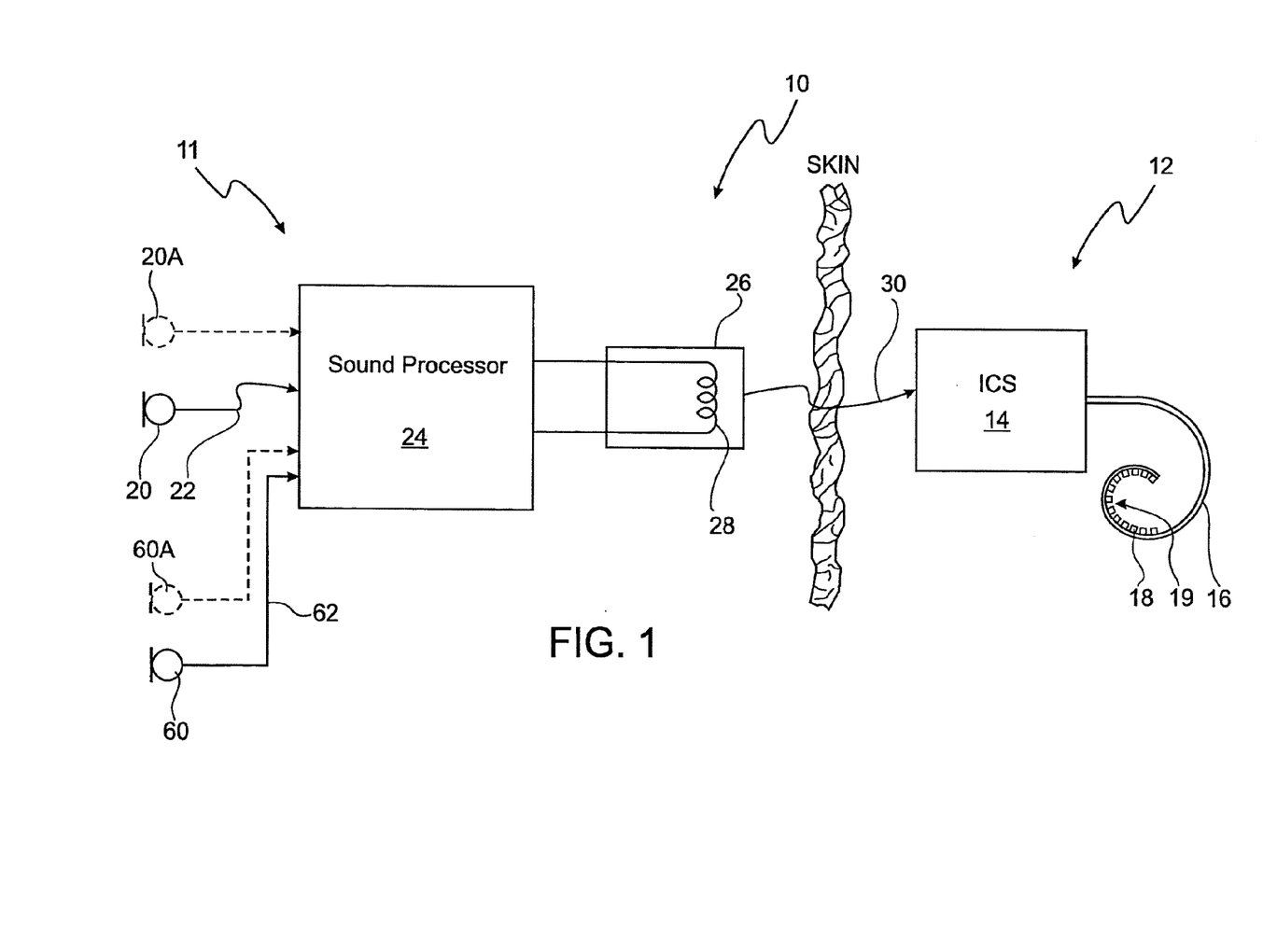
FIG. 1 is a schematic view of an example of a CI system according to the invention.

In FIG. 1 an example of a cochlear implant system 10 is shown schematically. The system comprises a sound processing sub-system 11 and a stimulation sub-system 12. The sound processing sub-system 11 serves to detect or sense an audio signal and divide the audio signal into a plurality of analysis channels each containing a frequency domain signal (or simply "signal") representative of a distinct frequency portion of the audio signal. A signal level value is determined for each analysis channel by analyzing the respective frequency domain signal. Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlear of a patient in accordance with the stimulation parameters received from the sound processing sub-system 11. Electrical stimulation is provided to the patient via a CI stimulation assembly 18 comprising a plurality of stimulation channels, wherein various known stimulation strategies, such as current steering stimulation or N-of-M stimulation, may be utilized.

As used herein, a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes.

As used herein, an "N-of-M stimulation strategy" is one in which stimulation current is only applied to N of M total stimulation channels during a particular stimulation frame, where N is less than M. An N-of-M stimulation strategy may be used to prevent irrelevant information contained within an audio signal from being presented to a CI user, achieve higher stimulation rates, minimize electrode interaction, and/or for any other reason as may serve a particular application.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

Figure 2:
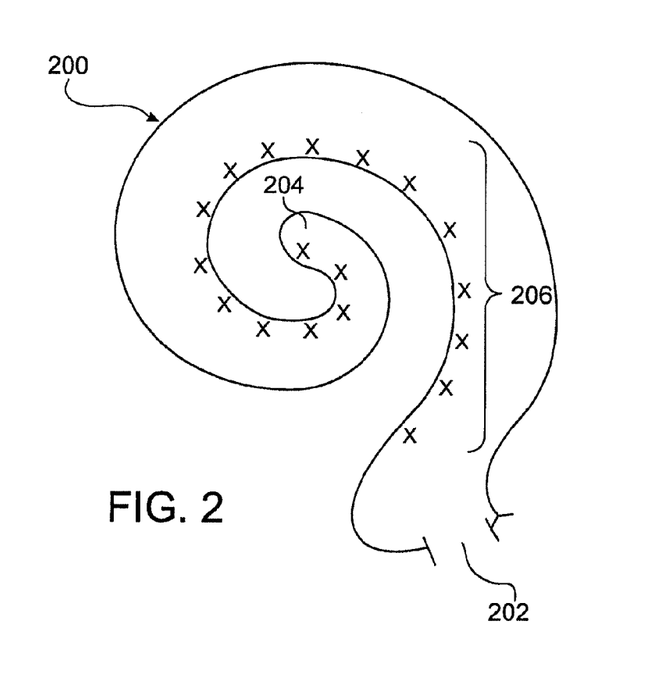
FIG. 2 is a schematic cross-sectional view of a human cochlea with marked stimulation sites.

FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 1, sound processing subsystem 11 and stimulation subsystem 12 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

In the example shown in FIG. 1, the stimulation sub-system 12 comprises an implantable cochlear stimulator ("ICS") 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 1, the sound processing sub-system 11 is designed to be located external to the patient; however, in alternative examples, at least one of the components of the sub-system 11 may be implantable.

In the example shown in FIG. 1, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 1, the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

The CI system 10 formed of the subsystems 11 and 12 is provided for a stimulation of the ipsilateral cochlea, with the microphone 20 being located at the ipsilateral ear. In addition to the microphone 20, which captures an ipsilateral audio signal from ambient sound reaching the ipsilateral ear, the system comprises a contralateral microphone 60 worn at the contralateral ear for capturing a contralateral audio signal from sound reaching the contralateral ear. The contralateral microphone 60 is adapted to transmit the contralateral audio signal via a wired or wireless link 62 to the sound processor 24. In the example of FIG. 1, the CI system is designed for unilateral stimulation of the patient's hearing via the ipsilateral ear, using audio signals both from the contralateral and the ipsilateral side of the head (as already mentioned above, such systems also are known as "CROS" systems).

Figure 3:
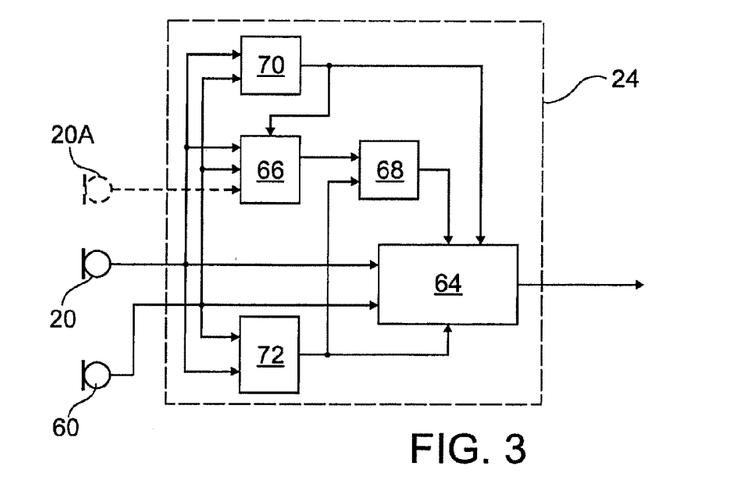
FIG. 3 is a block diagram of the signal processing structure of a CI system according to the invention.

A block diagram of an example of the sound processor 24 is schematically shown in FIG. 3, wherein both the ipsilateral audio signal from the ipsilateral microphone 20 and the contralateral audio signal from the contralateral microphone 60 are supplied to a signal processing unit 64 which generates the ipsilateral auditory nerve stimulation signal supplied to the ICS 14 from the ipsilateral audio signal and the contralateral audio signal. The sound processor 24 also comprises a direction of arrival (DOA) unit 66 for determining periodically a main direction of incidence of ambient sound from a sound source by analyzing the ipsilateral and contralateral audio signals. For example, the DOA may be determined in intervals of 10 ms. However, while determining the DOA in constant time intervals is preferred, the time intervals in principle also may differ from each other.

The output of the DOA unit 66 is provided to a directional information coding unit 68 for coding information concerning the determined main direction of incidence in the ipsilateral auditory nerve stimulation signal in a manner so as to render the directional information provided by the DOA unit perceivable by the patient in order to enable the patient to localize the sound source by ipsilateral cochlea stimulation. To this end, the coding unit 68 acts on the signal processing unit 64 in an appropriate manner so as to cause the signal processing unit 64 to process the audio signal/ stimulation signal in an appropriate manner, as will be explained in detail below.

The signal processing unit 64 may generate the ipsilateral auditory nerve stimulation signal from the ipsilateral audio signal alone or, as already mentioned above, from a combination of the ipsilateral and the contralateral audio signal.

In order to enable front/back discrimination of the direction of sound incidence at each side of the head at least two spaced apart microphones may be provided, rather than a single microphone at each side (such additional microphones are indicated at 20A and 60A in dashed line in FIG. 3, with the audio signals captured by these additional microphones then likewise being supplied to the DOA unit 60).

There are various options for encoding directional information in the auditory nerve stimulation signal.

According to one example, spectral filtering may be applied to the auditory nerve stimulation signal depending on the determined main direction of incidence. For example, a high pass tilt may be applied to the auditory nerve stimulation signal if the determined main direction of incidence is on one side (e.g., left side) of the head, and a low pass tilt may be applied if the determined main direction of incidence is on the other side (e.g. right side) of the head. Thus, the patient may perceive the direction of incidence via a change in the spectral/pitch perception. According to a variant, a band pass-like amplification may be applied to a certain spectral band selected according to the determined main direction of incidence. For example, the octave around 500 Hz may be amplified by 6 dB for sounds from the front, the octave around 100 Hz may be amplified for sounds from a direction of 45° with regard to the front direction, etc. Such approach requires a relearning of Blauert's directional bands (similar to a "Wah-Wah" effect). To achieve this, unambiguous spatial cues are required, which requires synchronized dynamic processing in bimodal or bilateral fittings.

According to another variant, an echo effect may be applied to the auditory nerve stimulation signal depending on the determined main direction of incidence. For example, a slight echo effect may be applied to the signal if the determined main direction of incidence is on a certain side (e.g. left side) of the head, e.g., on the contralateral side, whereas no echo effect is applied if the direction of incidence is on the other side of the head.

According to a further variant, a phase shifting may be applied to the auditory nerve stimulation signal depending on the determined main direction of incidence, wherein the delay or phase-shift is controlled by the direction of incidence. As a result, direction-dependent comb-filter or resonance effects are generated which can be used as spatial cues.

According to another variant, a speech sound may be added to the auditory nerve stimulation signal, with the meaning of the speech sound depending on the main direction of incidence; for example, the meaning of the speech sound may be directly indicative of the main direction of incidence. Thus, a soft speech sound may be added to the signal whispering the direction of sound incidence, e.g., "front", "back", "left/back", etc.

According to a further embodiment, the auditory nerve stimulation signal may be changed in a manner so as to stimulate or enhance the direction-dependent filtering of the pinna. For example, in case of a BTE type speech processor any other processor which does not pick up the sound in the ear channel or at the entrance of the ear channel (e.g., a "button processor"), the pinna effect may first be simulated and then be enhanced.

In general, ambient sound may result from multiple sound sources, for example multiple talkers or a talker and background noise. Thus, the sound processor 24 may comprise a sound source separation unit 70 which is adapted to distinguish, by analyzing the ipsilateral and the contralateral audio signal, multiple sound source contributing simultaneously to the ipsilateral and contralateral audio signal and to determine one of the sound sources as a target sound source, with the direction of incidence of sound from the target sound source being taken as the main direction of incidence which is used by the coding unit 68. For example, the source separation unit 70 may be adapted to determine whether one of the sound sources is a speech source, with the speech source being taken as the target source. In case that more than one source has a speech-like character, the sound source having the most pronounced speech-like characteristic may be taken as the target source.

The source separation unit 70 may comprise a signal to noise (SNR) estimator for determining time windows and frequency windows in which speech is dominant, with the directional code only being applied to these windows. This allows a better perceptual segregation of auditory streams and thus will improve speech understanding in noise.

Alternatively, the source separation unit 70 may comprise a blind source separation (BSS) unit for separating the sound sources present in the ambient sound. Also in this case, the loudest and/or most speech-like sound source may be taken as the target source according to which the directional code is applied.

Preferably, the sound processor 24 also comprises a classifier unit 72 for determining a present audio scene from a given plurality of auditory scenes by analyzing the ipsilateral and contralateral audio signal. In this case the coding unit 68 may be adapted to provide for an alarm signal in the auditory nerve stimulation signal when the determined present auditory scene is classified at dangerous. For example, if it is determined that a sound source, such as a car, approaches the patient from behind, a respective alarm signal may be issued. According to one example, such alarm signal may be a speech signal having a meaning corresponding to the determined auditory scene.

While the invention is particularly useful for unilateral cochlea stimulation, such as the CROS configuration of FIG. 1, the invention also may be applied to bimodal or bilateral stimulation.

Figure 5:
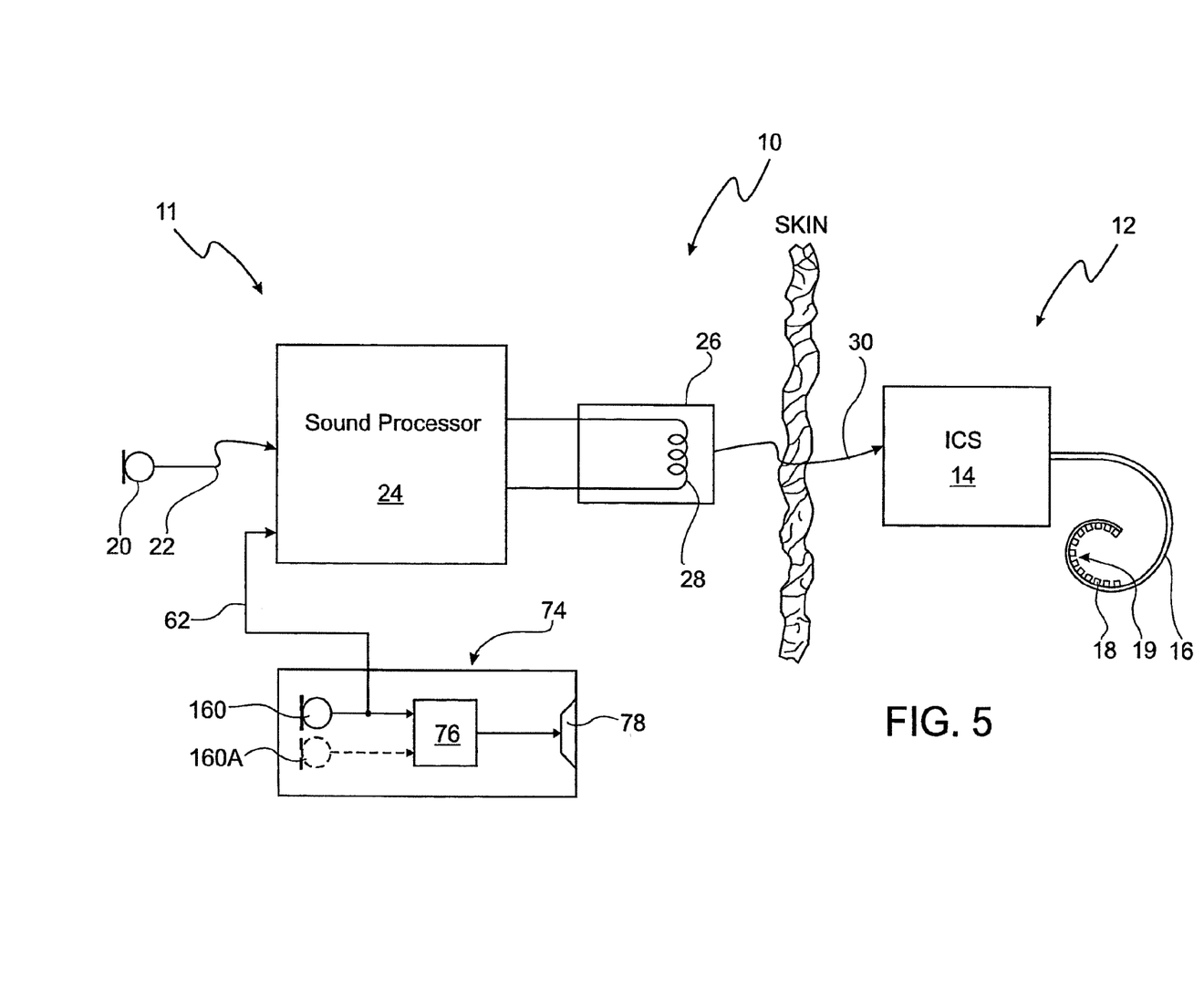
FIG. 5 is a view like FIG. 1, wherein an alternative example is shown.

An example of bimodal stimulation is shown in FIG. 5, wherein a hearing aid 74 is worn at the contralateral ear, comprising a microphone 160 for capturing contralateral audio signals from ambient sound reaching the contralateral ear, an audio signal processing unit 76 processing the captured audio signals and an electroacoustic output transducer 78 for supplying sound generated from the processed audio signals to the contralateral ear. The hearing aid 74 is adapted to provide the captured contralateral audio signals via a link 62, which may be wired or wireless, to the sound processor 24 of the ipsilateral CI system. In such embodiments, the hearing aid microphone 160, which also may be implemented as a plurality of spaced apart microphones for enabling front/back discrimination (e.g. including one additional microphone 160A as indicated in dashed lines), takes the role of the CROS microphone 60 of the embodiment of FIG. 1.

Figure 6:
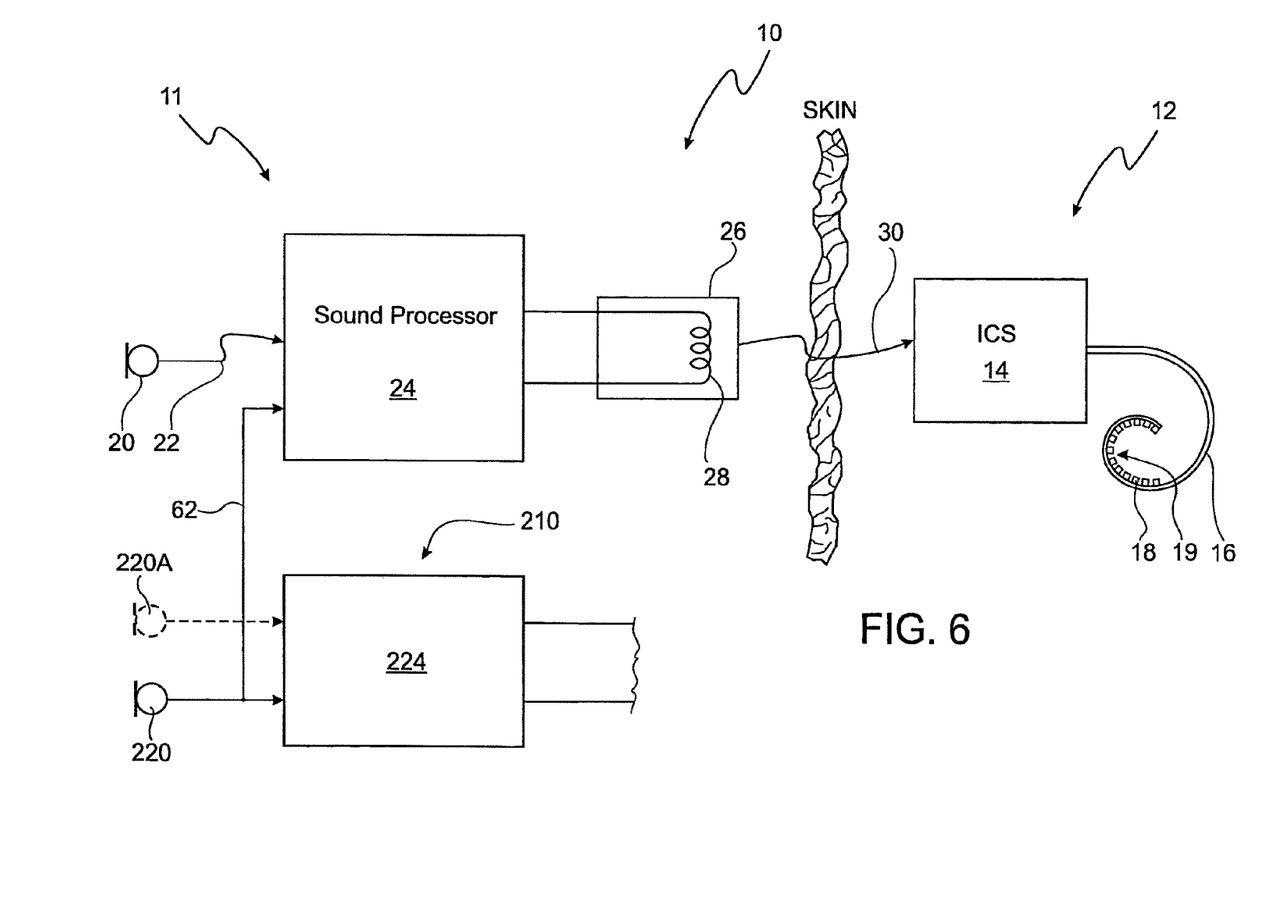
FIG. 6 is a view like FIG. 1, wherein a further alternative example is shown.

An example of a bilateral CI fitting is shown in FIG. 6, wherein the contralateral ear is fitted with a contralateral CI system 210 which is similar or identical to the ipsilateral CI system 10 and comprises a microphone 220 for capturing contralateral audio signals from ambient sound reaching the contralateral ear (and other components, such as a sound processor 224, etc.). The contralateral CI system 210 is adapted to supply the contralateral audio signal to the sound processor 24 of the ipsilateral CI system 10 via a link 62 which may be wired or wireless. The contralateral CI system 210 may be provided with a second microphone 220A for enabling front/back discrimination. The microphone 220 of the contralateral CI system 210 takes the role of the contralateral microphone 60 of the CROS system shown in FIG. 1. According to one example, the ipsilateral CI system 10 may be adapted to supply the ipsilateral audio signals captured by the microphone 20 to the contralateral CI system 210 via a link 262. In bilateral designs also the contralateral CI system 210 may apply directional coding to the contralateral auditory nerve stimulation signal.

According to a further variant, the ipsilateral CI system 10 in all cases may be replaced by a hybrid system comprising a CI device and a hearing aid on the same, i.e. ipsilateral, ear in order to provide additional acoustic stimulation to the ipsilateral ear.

Figure 4:
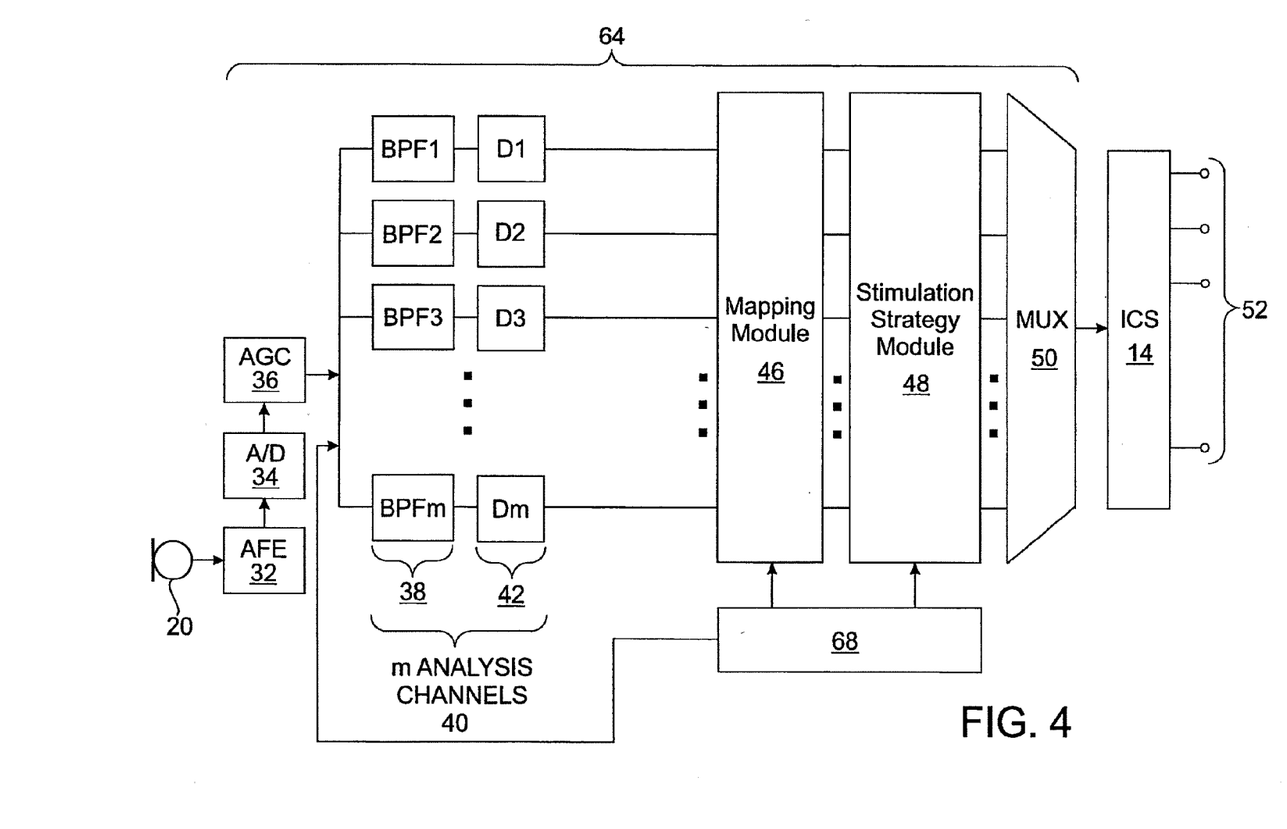
FIG. 4 is a more detailed block diagram of a part of the signal processing structure of the example of FIG. 3.

In FIG. 4, a schematic example of the signal processing unit 64 is shown. The ipsilateral audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36. In addition, also the contralateral audio signals captured e.g. by the CROS microphone 60 (or the contralateral microphones 160, 220) may be supplied to the processing unit 64 (this option is not shown in FIG. 4).

After appropriate automatic gain control, the digital signal is subjected to a filter bank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then divide the resulting frequency bins into the analysis channels 40.

The signals within each analysis channel 40 are input into an envelope detector 42 in order to determine the amount of energy contained within each of the signals within the analysis channels 40.

The output signals of the envelope detector 42 are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient by the ICS 14 via M stimulation channels 52. For example, each of the m stimulation channels 52 may be associated to one of the stimulation contacts 19 or to a group of the stimulation contacts 19. Such mapping concerns both amplitude mapping, the acoustic sound level in an analysis channel is mapped to an electric amplitude in the stimulation channel (e.g., to a certain stimulation current level) and allocation of a certain frequency range to a certain stimulation site/electrode (i.e., allocation of a certain analysis channel to a certain stimulation channel). Both kinds of mapping may be achieved by the same mapping module 46 or by separate mapping modules (not shown).

The signal processing unit 64 further comprises a stimulation strategy module 48 which serves to generate one or more stimulation parameters based on the output signals of the envelope detector 42 and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The signal processing unit 64 also comprises a multiplexer 50 which serves to serialize the stimulation parameters generated by the stimulation strategy module 48 so that they can be transmitted to the ICS 14 via the communication link 30, i.e., via the coil 28.

The signal processing unit 64 may operate in accordance with at least one control parameter. Such control parameters may be the most comfortable listening current levels (MCL), also referred to as "M levels", threshold current levels (also referred to as "T levels"), dynamic range parameters, channel acoustic gain parameters, front and back end dynamic range parameters, AGC parameters, current steering parameters, amplitude values, pulse rate values, pulse width values, polarity values and/or filter characteristics. Examples of such processing units can be found, for example, in International Patent Application Publication WO 2011/032021 A1 and corresponding U.S. Pat. No. 8,422,706.

In order to implement the directional coding of the auditory nerve stimulation signal, the coding unit 68 may act in an appropriate manner, for example, on the mapping module 46 and/or the stimulation strategy module 48, and/or it may supply an audio signal (for directional coding by speech) which added to the audio signal of the microphone 20.

The classifier unit 72, if present, may also act on the modules 46 and 48.

What is claimed is:

1. A system for stimulation of a patient's ipsilateral cochlea, comprising
   at least two spaced apart microphones configured to be worn by the patient and configured to provide a first input audio signal and a second audio signal from ambient sound, respectively;
   a sound processor configured to generate an ipsilateral auditory nerve stimulation signal in a plurality of output channels from at least one of the input audio signals; and
   a stimulation assembly configured to be implanted within the ipsilateral cochlea and having a plurality of stimulation channels for ipsilateral stimulation of the patient's hearing according to the ipsilateral auditory nerve stimulation signal,
   the sound processor comprising
   a direction of arrival (DOA) unit configured to periodically determine a main direction of incidence of ambient sound from a sound source by analyzing the first and second audio signals, and
   a directional information coding unit configured to code information concerning the determined main direction of incidence in the ipsilateral auditory nerve stimulation signal in manner so as to render said directional information perceivable by the patient in order to enable the patient to localize the sound source by ipsilateral cochlear stimulation;
   the directional information coding unit configured to code the information concerning the determined main direction of incidence in the ipsilateral auditory nerve stimulation signal by
       applying a spectral filtering to the ipsilateral auditory nerve stimulation signal depending on the determined main direction of incidence,
       applying an echo effect to the ipsilateral auditory nerve stimulation signal depending on the determined main direction of incidence,
       applying a phase-shifting to the ipsilateral auditory nerve stimulation signal depending on the determined main direction of incidence, or
       adding a speech sound to the ipsilateral auditory nerve stimulation signal, with a meaning of the speech sound depending on the determined main direction of incidence.

2. The system of claim 1, wherein at least one of the microphones is adapted to be worn at each of two sides of the head of the patient in order to capture an ipsilateral audio signal as said first audio signal and a contralateral audio signal as said second audio signal.

3. The system of claim 2, wherein the sound processor is designed to be worn at the ipsilateral side of the head of the patient, and wherein the at least one microphone adapted to be worn at the contralateral side of the head is adapted to transmit the contralateral audio signal to the sound processor via a wired or wireless link.

4. The system of claim 2, wherein the sound processor is adapted to generate the ipsilateral auditory nerve stimulation signal from the ipsilateral audio signal alone or from a combination of the ipsilateral audio signal and the contralateral audio signal.

5. The system of claim 2, wherein at least two of the at least two spaced apart microphones are adapted to be worn at the ipsilateral side of the head and at least two of the at least two spaced apart microphones are adapted to be worn at the contralateral side of the head in order to enable front/back discrimination of the direction of incidence.

6. The system of claim 1, wherein the system is designed for unilateral stimulation via the ipsilateral ear.

7. The system of claim 1, wherein the system further comprises an electroacoustic hearing aid for acoustic stimulation of the contralateral ear, and wherein the at least one contralateral microphone forms part of the hearing aid.

8. The system of claim 7, wherein the hearing aid is adapted to transmit the contralateral audio signal via a wireless link to the sound processor.

9. The system of claim 1, wherein the system further comprises
   a second sound processor adapted to be worn at the contralateral side of the head of the patient and configured to generate a contralateral auditory nerve stimulation signal in a plurality of output channels from at least one of the first and second input audio signals; and
   a second stimulation assembly adapted to be implanted within the contralateral cochlea and having a plurality of stimulation channels for contralateral stimulation of the patient's hearing according to the contralateral auditory nerve stimulation signal.

10. The system of claim 9, wherein the second sound processor comprises a directional information coding unit configured to code information concerning the determined main direction of incidence in the contralateral auditory nerve stimulation signal in manner so as to render said directional information perceivable by the patient in order to enable the patient to localize the sound source by contralateral cochlear stimulation.

11. The system of claim 1, wherein the applying of the spectral filtering comprises applying a high pass tilt to the ipsilateral auditory nerve stimulation signal if the determined main direction of incidence is on one side of the head and to apply a low pass tilt to the ipsilateral auditory nerve stimulation signal if the determined main direction of incidence is on the other side of the head.

12. The system of claim 1, wherein the applying of the spectral filtering comprises applying a bandpass-like amplification to a certain spectral band, with said certain spectral band being selected according to the determined main direction of incidence.

13. The system of claim 1, wherein the applying of the echo effect comprises applying an echo effect to the ipsilateral auditory nerve stimulation signal only if the determined main direction of incidence is on a certain side of the head.

14. The system of claim 1, wherein a meaning of the speech sound is indicative of the determined main direction of incidence.

15. The system of claim 1, wherein the directional information coding unit is further configured to code the information concerning the determined main direction of incidence in the ipsilateral auditory nerve stimulation signal by changing the ipsilateral auditory nerve stimulation signal in manner so as to simulate or enhance the direction dependent filtering of the pinna.

16. The system of claim 1, wherein the sound processor is adapted to distinguish, by analyzing the first and second audio signals, multiple sources contributing simultaneously to the first and second audio signals and to determine one of the sound sources as a target sound source, wherein the direction of incidence of sound from the target sound source is taken as said main direction of incidence.

17. The system of claim 16, wherein sound processor is adapted to determine whether one of the determined sound sources is a speech source, wherein the speech source is taken as the target source.

18. The system of claim 17, wherein the sound processor comprises an SNR (signal to noise) estimator configured to determine time and frequency windows in which speech is present.

19. The system of claim 16, wherein the sound processor comprises a BSS (blind source separation) unit configured to separate the sound sources.

20. The system of claim 16, wherein the sound processor is adapted to select the sound source having the highest level as the target source.

21. The system of claim 16, wherein the sound processor is adapted to select the sound source having most speech-like character as the target source.

22. The system of claim 1, wherein the sound processor comprises a classifier unit configured to determine a present auditory scene from a plurality of auditory scenes by analyzing the first and second audio signals, and wherein the directional information coding unit is adapted to provide an alarm signal in the ipsilateral auditory nerve stimulation signal in case that the determined present auditory scene is classified as a dangerous.

23. The system of claim 22, wherein the alarm signal is a speech signal.

24. The system of claim 1, wherein the implantable stimulation assembly comprises a plurality of stimulation electrodes, and wherein each stimulation channel is attributed to at least one of the stimulation electrodes.

25. A method for stimulation of a patient's cochlea, comprising
providing a first input audio signal and a second audio signal from ambient sound by at least two spaced apart microphones worn by the patient,
generating, by a sound processor, an ipsilateral auditory nerve stimulation signal in a plurality of output channels from at least one of the input audio signals,
periodically determining, by a sound processor connected to the at least two spaced apart microphones, a main direction of incidence of ambient sound from a sound source by analyzing the first and second audio signals,
coding, by the sound processor, information concerning the determined main direction of incidence in the ipsilateral auditory nerve stimulation signal in manner so as to render said directional information perceivable by the patient in order to enable the patient to localize the sound source by ipsilateral cochlear stimulation, and
stimulating the patient's hearing according to the ipsilateral auditory nerve stimulation signal via a stimulation assembly implanted within the ipsilateral cochlea and having a plurality of stimulation channels;
the coding of the information concerning the determined main direction of incidence in the ipsilateral auditory nerve stimulation signal comprising
applying a spectral filtering to the ipsilateral auditory nerve stimulation signal depending on the determined main direction of incidence,
applying an echo effect to the ipsilateral auditory nerve stimulation signal depending on the determined main direction of incidence,
applying a phase-shifting to the ipsilateral auditory nerve stimulation signal depending on the determined main direction of incidence, or
adding a speech sound to the ipsilateral auditory nerve stimulation signal, with a meaning of the speech sound depending on the determined main direction of incidence.

26. The method of claim 25, wherein the applying of the spectral filtering comprises applying a high pass tilt to the ipsilateral auditory nerve stimulation signal if the determined main direction of incidence is on one side of the head and to apply a low pass tilt to the ipsilateral auditory nerve stimulation signal if the determined main direction of incidence is on the other side of the head.

27. The method of claim 25, wherein the applying of the spectral filtering comprises applying a bandpass-like amplification to a certain spectral band, with said certain spectral band being selected according to the determined main direction of incidence.

28. The method of claim 25, wherein the applying of the echo effect comprises applying an echo effect to the ipsilateral auditory nerve stimulation signal only if the determined main direction of incidence is on a certain side of the head.

* * * * *